(12) United States Patent
Yang

(10) Patent No.: US 6,373,576 B1
(45) Date of Patent: Apr. 16, 2002

(54) METHOD FOR MEASURING CONCENTRATIONS OF DOPANTS IN A LIQUID CARRIER ON A WAFER SURFACE

(75) Inventor: Jiunn Der Yang, Hsin-Chu (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 0 days.

(21) Appl. No.: 09/459,728

(22) Filed: Dec. 13, 1999

(51) Int. Cl.$^7$ .............................................. G01N 21/55
(52) U.S. Cl. ..................... 356/445; 356/388; 356/389; 250/581
(58) Field of Search ................................ 356/445, 388, 356/389, 432, 434, 435, 436; 250/581

(56) References Cited

U.S. PATENT DOCUMENTS

| | | | |
|---|---|---|---|
| 4,845,373 A | 7/1989 | Jamieson | 250/548 |
| 4,877,326 A | 10/1989 | Chadwick et al. | 356/394 |
| 6,048,742 A * | 4/2000 | Weyburne et al. | 438/7 |

* cited by examiner

*Primary Examiner*—Frank G. Font
*Assistant Examiner*—Roy M. Punnoose
(74) *Attorney, Agent, or Firm*—George O. Saile; Stephen B. Ackerman; William Robertson

(57) ABSTRACT

A method for non-destructively testing for the concentration of a component of a film that is used for doping a region of a semiconductor wafer uses an image histogram of the light reflected from an array of points on the film and the underlying substrate. The image histogram has peaks that are characteristic of the composition of the film. Tests are run to establish the image histogram peaks for a film with a normal concentration of the components and for films with low and high concentrations. When the same test is made for the film of a production wafer, the concentration of the component is readily classified as normal, high, or low.

10 Claims, 3 Drawing Sheets

METHOD FOR MEASURING CONCENTRATIONS OF DOPANTS IN A LIQUID CARRIER ON A WAFER SURFACE

FIELD OF THE INVENTION

This invention relates generally to processing a semiconductor wafer to form circuit devices and more specifically it relates to a method for testing a liquid spread on the surface of the wafer to measure the concentration of dopants in the liquid.

INTRODUCTION

In one step of a familiar process for manufacturing circuit devices in a semiconductor wafer, a thin film of a liquid called BPTEOS is deposited on the surface of a wafer. In this abbreviation, the letters B and P stand for components of the liquid which will become impurities or dopants in the wafer. More specifically, P stands for a compound containing a group V element, phosphorous, and B stands for a compound containing a group III element, boron. The preferred components are $P_2O_3$ or $P_2O_5$ and $B_2O_3$.

It would be advantageous to measure the concentration of the B and P components of a film on a relative scale. For example a three part scale corresponds to the common terms normal, low and high and a two part scale corresponds to normal and high (or normal and low).

The terms high and low are defined by their adverse effect on the wafer. For example, a high concentration would cause B and P precipitation during a high temperature treatment of the wafer in a subsequent processing step.

THE PRIOR ART

In one known measurement system, a BPTEOS film is irradiated with x-rays and the intensity and wavelength of the radiation that is emitted by the film is measured. The concentrations of the P and B components can be inferred from the intensity and wavelength because they are characteristic of these atoms.

The x-ray technique cannot be used on a production wafer because the energy of the x-ray can damage devices formed on the wafer. The x-ray technique has an additional limitation that it is not very sensitive for the B component.

In another measurement system, the film is irradiated with infra red light and the reflected light is analyzed. The technique is called FTIR from the fact that it produces a Fourier transform of the reflected infra red light. FTIR has low sensitivity for the P component ($P_2O_3$).

SUMMARY OF THE INVENTION

One object of my invention to provide a new and improved method for non-destructively measuring the concentrations of the B and P components for a production wafer.

I have found that an image histogram for light reflected from a BPTEOS film is characteristic of the relative concentrations of the B and P components.

In a preliminary step, a film is formed on a dummy wafer and the components are measured in this film, using any suitable technique such as the prior art techniques already described. (A destructive test can be used on the test wafer.)

The film and the underlying surface of a test wafer are then illuminated at an array of points and the intensity of reflected light from these points is recorded. The light intensity can be described with a histogram, and an image histogram is a plot of intensity over the range of values. An image histogram has peaks that are characteristic of the concentration of the B and P components of the film. A commercially available machine produces the image histogram.

The test is performed with a normal concentration and with high and/or low concentrations. This data can then be used for production wafers to the extent that the conditions are the same.

Later, a production wafer is tested in the same way and its film is characterized by comparison with the test data.

The histogram also depends on other factors, the thickness of the film and the underlying pattern of the wafer, which I control within suitable limits. As a specific example, I control the film thickness so that its variations are less than 5%.

Other objects and features of the invention will appear in the description of a preferred embodiment.

THE DRAWING

THE PREFERRED EMBODIMENT

The Preferred Testing Apparatus

My novel test method uses a commercially available wafer testing apparatus that is manufactured by the KLA Instrument Corporation. The invention is not limited to using this particular apparatus, and the apparatus will be described in terms of the functions used in our test. These functions can be performed by other apparatus or by a apparatus constructed to provide these functions.

Figure 1:
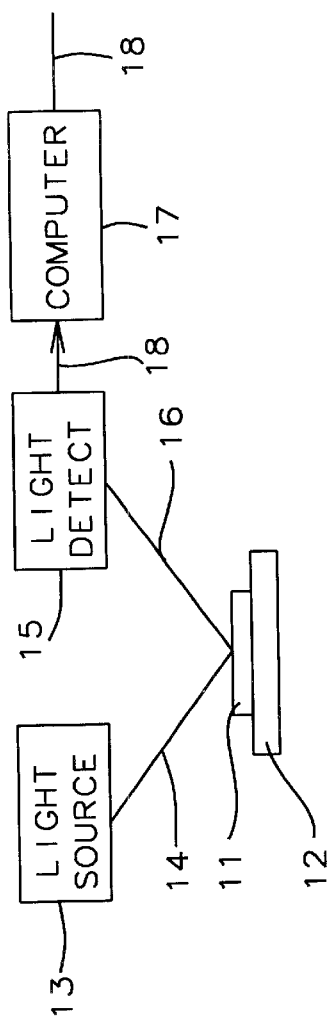
FIG. 1 is a diagram of the preferred apparatus used in my test.

FIG. 1 shows the wafer substrate 11 carried on a support 12 of the test apparatus. The apparatus has a monochromatic light source 13 that directs light to the substrate along a path 14 and a light detector 15 that receives reflected light along a path 16. A computer 17 receives an input 18 from the detector 15 and produces an output 18. The output is commonly a display on a computer monitor, for example FIGS. 3A and 3B.

One available output is a digitized image. The imaged field of the wafer is presented as rectangular array of image points (pixels) that are analogous to the familiar array of pixels on a small section of a commercial color television screen.

In an example being described, the apparatus presents a value in the range 0 to 255 for each pixel. (This range can be represented in a computer by an eight bit byte of information.) The pixel values represent the intensity of reflected light at the wavelength of monochromatic light source 13 and are called gray scale values.

The preferred test apparatus produces a pixel array (called a frame) that is 2048 pixels high and 512 pixels wide. Stated differently, the array of pixels has 2048 columns and 512 rows. This specific array size is given here simply to make the description easier to understand, and it will be a simple matter for one skilled in the art to generalize the array size and other details of this apparatus.

In the exemplary apparatus, a pixel represents a square on the wafer surface that is a few tenths of a micron on a side, preferably 0.62 $\mu$m. Thus the area being sampled is small but it can include a pattern of device features that varies according to the location of the image on the wafer. As will be explained later, the particular pattern affects the intensity of the reflected light.

The apparatus also produces a histogram of the information in the pixel array. The 256 possible values of the pixels are grouped in convenient ranges and, as in other histograms, the number of pixels in each range is displayed by the height of a bar. A histogram is a common device for displaying information, and the KLA apparatus commonly displays the histogram and the digitized image together.

The KLA apparatus also produces a plot, called an image histogram, that has the values 0 to 255 along the horizontal axis and the frequency of these values along the vertical axis. (The vertical axis has the statistical frequency and not the frequency of the reflected light.)

For a large number of sample points, the image histogram is smooth and does not display jumps between discrete values of a conventional histogram using a series of vertical bars.

The apparatus has a single line of light sensors. The number of these sensors establishes the number of pixels in a column of the array (2048, as explained earlier). The chip surface is scanned with a relative motion between the light sensors and the chip, and the light received by each detector is recorded. (In the specific apparatus, the chip is moved and the apparatus is stationary.) The number of pixels in a row of the array (512) is established by this scanning motion.

An Example: FIGS. 2A–2F

Figure 2A:
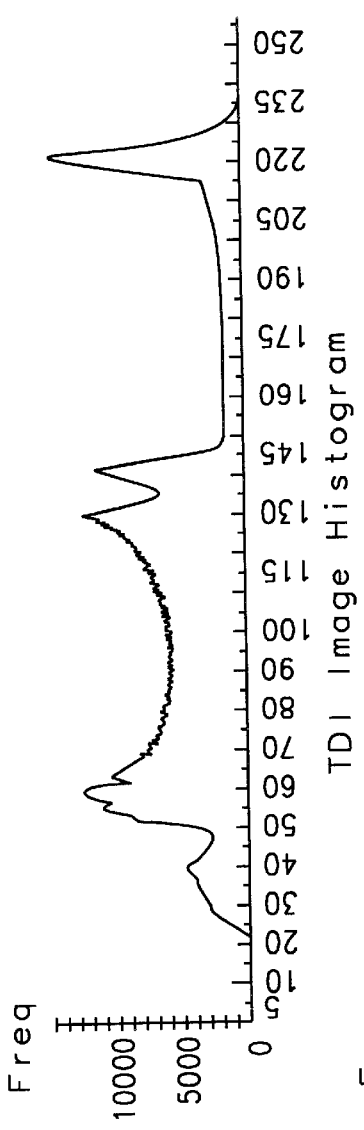
FIGS. 2A–2F are image histograms different films on the surface of a test wafer.

FIG. 2A is the image histogram for a film without the B or P components. (USG stands for undoped silicon glass, pure $SiO_2$ glass.) This image histogram illustrates characteristics that are typical of all of the image histograms. Note for example that the sample frequency (on the vertical axis) is about zero for samples with a light intensity between zero and about twenty. A simplified interpretation is that all of the sample positions on the surface of the test wafer reflected at least this small amount of light.

Also note that the sample frequency has intensities for which the sample frequencies rises or falls sharply and intensities for which it is relatively flat or varies only slowly as a function of intensity.

It is an important advantage of my test that the image histograms can be distinguished on the basis of only a few peaks. (When the test is repeated for the same film and underlying pattern, the peaks are unchanged.) The characteristic that distinguishes the test film of FIG. 1A is the sample frequency peaks at an intensity of 60, 128, 142, and 220 on the gray scale.

The absolute values of these peaks depend in part on the brightness of the wafer surface and a wafer of a different design or a different location on the test wafer or on similar wafers will ordinarily give different values for the peaks. As will be apparent from the discussion later, it is a simple matter to create the test data for a given wafer design and to use this data for testing the film of wafers of the same design (or more specifically, the same underlying pattern).

The KLA apparatus provides the peaks directly and this feature of the preferred test apparatus makes my test particularly advantageous in a film test for a production line.

Figure 2B:
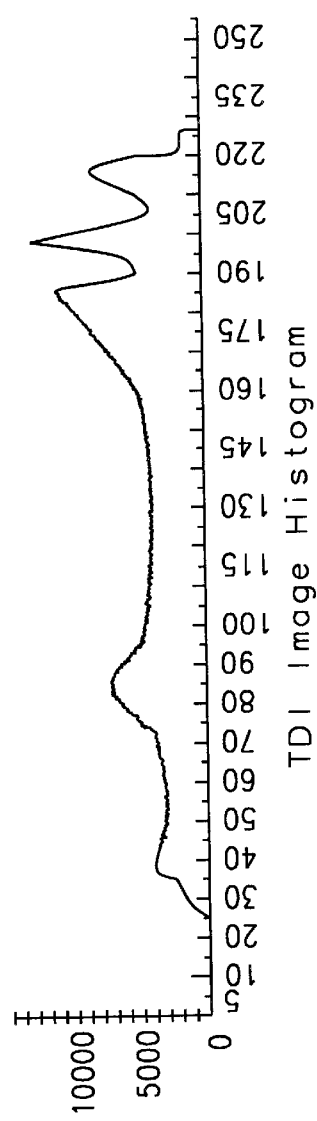

FIG. 2B is the image histogram for normal BPTEOS. Normal BPTEOS has the concentrations of the B and P components that are normally used for production wafers. Note the sample frequency peaks at about 85, 186, 200 and 215 on the gray scale.

Figure 2C:
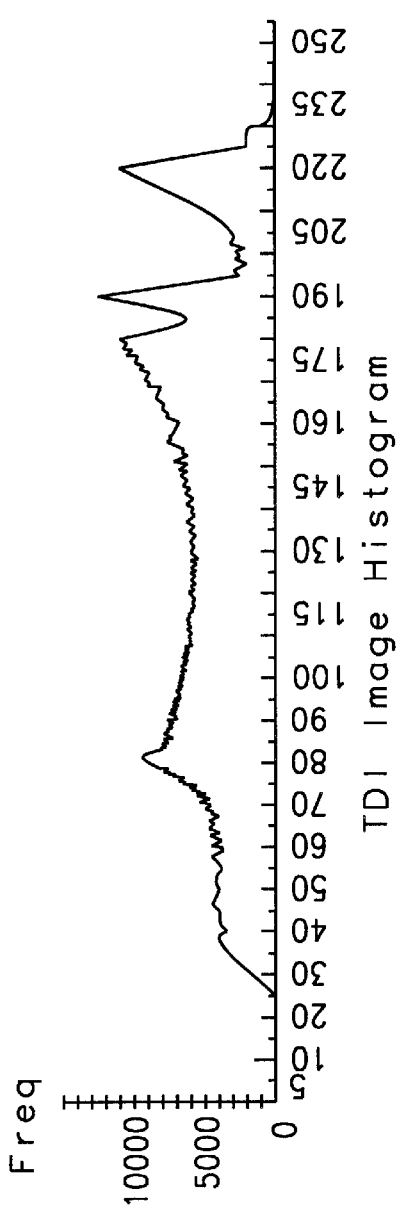

FIG. 2C is the image histogram for normal highly doped BPTEOS. BPTEOS. Note the sample frequency peaks at about 85, 177, 190, and 218 on the gray scale.

Figure 2D:
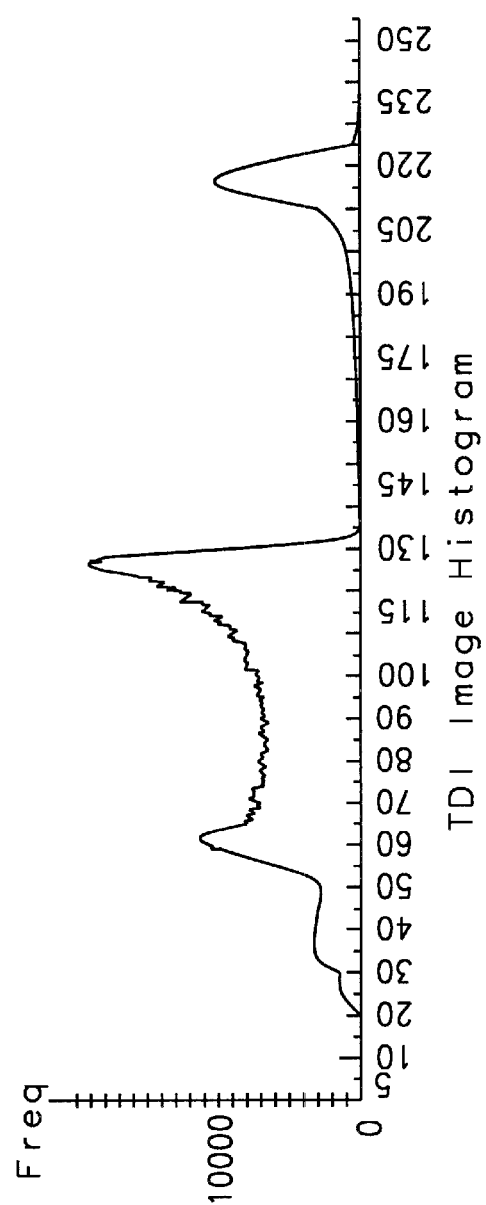

FIG. 2D is the image histogram for USG flow. It has sample frequency peaks of 60, 122, 127, and 218 on the gray scale.

Figure 2E:
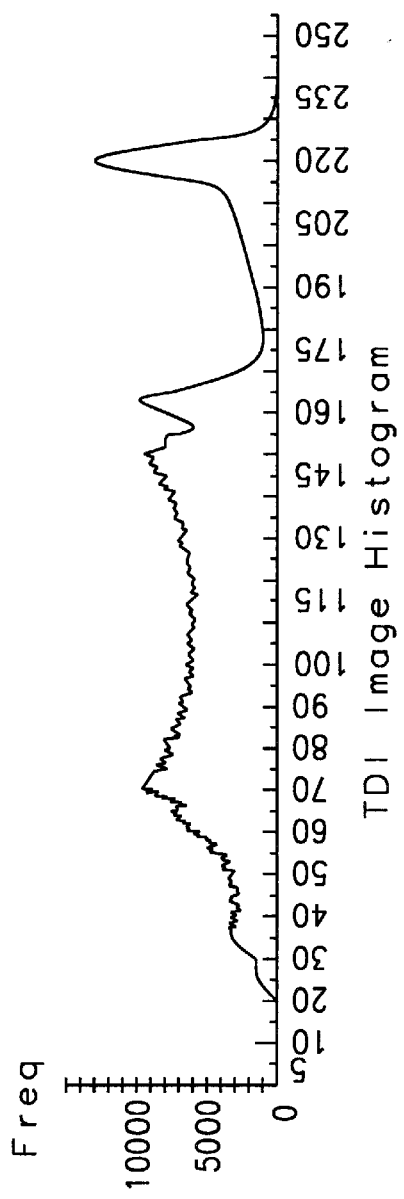

FIG. 2E is the image histogram for normal BPTEOS flow. (These materials flow in a high temperature operation to make the surfaces planar.) It has sample frequency peaks at about 70, 151, 163, and 219 on the gray scale.

Figure 2F:
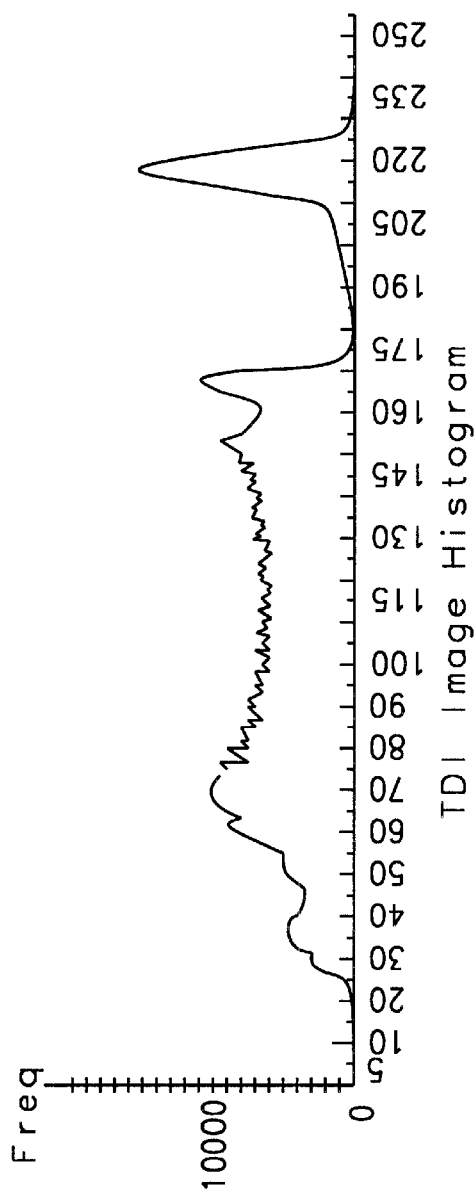

FIG. 2F is the image histogram for highly doped BPTEOS flow.

It has sample frequency peaks at about 70, 152, 166, and 220 on the gray scale.

A Production Wafer Test

As already explained, the results depend on the wafer pattern underlying the film. Although the test data given here describes a particular wafer and film, it illustrates that the test data can be generated easily and that the corresponding data for a production wafer can be easily created and accurately interpreted.

The test data was developed for a film of a thickness expected in wafer production. I have found that the test results do not change appreciably if the film thickness is within 5% of the film thickness for the test data.

The brightness of the wafer surface also affects the test results. Accordingly, the image histograms can differ for different locations on the same wafer or for corresponding positions of otherwise similar wafers of different generations.

Summary

From the description of a preferred embodiment of the invention, those skilled in the art will recognize variations within the skill or the art and the spirit of the invention.

What is claimed is:

1. A method for representing the concentration of a component of a film used in the manufacture of a semiconductor device, comprising, forming a predetermined thickness of the film on a surface of a semiconductor test wafer, wherein the film component is a compound containing a group III or a group V element, the film having a first known concentration of the component, the wafer surface having a pattern underlying the film that affects the intensity of light reflected from the wafer, detecting monochromatic light reflected from an array of points on the wafer surface in the region of the pattern, assigning an integer value to the intensity of the reflected light for each point, forming an initial image histogram for the integer values of the intensity of the reflected light, and recording the peaks of the image histogram for characterizing the concentration of the component of the film formed on the underlying pattern.

2. The method of claim 1 wherein the group III or a group V element is for use as a dopant in the manufacture of the semiconductor device.

3. The method of claim 2 wherein the compound is selected from the group comprising $P_2O_3$, $P_2O_5$, and $B_2O_3$.

4. The method of claim 2 including the subsequent steps of performing the same test with a second known concentration of the component, the first and second concentrations representing a normal concentration and a concentration that is known to be higher or lower than the normal concentration.

5. The method of claim 4 including the subsequent steps of performing the same test with a third known concentration of the component, the first, second, and third concentrations representing a normal concentration, a concentration that is known to be higher than the normal concentration, and a concentration that is known to be lower than the normal concentration.

6. The method of claim 4 further including the following subsequent steps, selecting a production wafer having the pattern of the test wafer, forming a film containing the component on the production wafer, detecting reflected monochromatic light from the region of the pattern, assigning an integer value to the light intensity and forming an image histogram as defined in claim 4 for the test wafer, and comparing the peaks of the image histogram for the production wafer with the previously recorded image histogram peaks to characterize the concentration of the component of the film on the production wafer with respect to the known concentration of the component for the production wafer.

7. The method of claim 6 wherein the characterization of the component is normal or high.

8. The method of claim 7 wherein the characterization of the component is normal, high or low.

9. A method for testing a film on the surface of a semiconductor wafer for the concentration of a component that will form an impurity in the wafer, wherein the film component is a compound containing a group III or a group V element for use as the impurity, comprising the following steps, selecting a production wafer having a film of a predetermined thickness, the wafer having a region with a predetermined pattern underlying the film, illuminating the region of the predetermined pattern with monochromatic light and scanning the illuminated surface with a detector and detecting the intensity of light reflected from an array of sample points on the surface and assigning an integral value to the light intensity of each sample point, forming an image histogram of the sample points representing the sample frequency of the light intensity in a gray scale, comparing the peaks of the image histogram with the peaks of image histograms formed by the same method on a plurality of test wafer films having substantially said predetermined thickness and each having a known concentration of the component, one of the known concentrations being a normal concentration and one other concentration being a high concentration, and characterizing the production film as normal or high.

10. The method of claim 9 wherein the step of comparing the peaks of the image histogram includes comparing the peaks of the image histogram with the peaks of image histograms for a normal concentration, a high concentration, and a low concentration, and wherein the step of characterizing the production film comprises characterizing the production film as normal, high or low.

* * * * *